US011937595B2

(12) United States Patent
Gao

(10) Patent No.: US 11,937,595 B2
(45) Date of Patent: Mar. 26, 2024

(54) AIR SUPPLY DEVICE WITH AIR REFRESHING AND MOSQUITO REPELLING FUNCTION

(71) Applicant: Shenzhen Sunzone Electrical Appliances Ltd., Shenzhen (CN)

(72) Inventor: Tianyu Gao, Shenzhen (CN)

( * ) Notice: Subject to any disclaimer, the term of this patent is extended or adjusted under 35 U.S.C. 154(b) by 929 days.

(21) Appl. No.: 16/883,923

(22) Filed: May 26, 2020

(65) Prior Publication Data

US 2021/0161120 A1 Jun. 3, 2021

(30) Foreign Application Priority Data

Dec. 3, 2019 (CN) .......................... 201911216716.4

(51) Int. Cl.
*A01M 29/12* (2011.01)
*A61L 9/03* (2006.01)
*F24H 3/04* (2022.01)

(52) U.S. Cl.
CPC ............. *A01M 29/12* (2013.01); *A61L 9/032* (2013.01); *F24H 3/0411* (2013.01); *A61L 2209/133* (2013.01); *A61L 2209/134* (2013.01)

(58) Field of Classification Search
CPC .. A01M 29/12; A61L 9/032; A61L 2209/133; A61L 2209/134; F24H 3/0411
USPC ........................................................ 392/386
See application file for complete search history.

(56) References Cited

U.S. PATENT DOCUMENTS

| 4,737,616 A | * | 4/1988 | Wen-Ying | ............. | F24H 9/1872 |
| | | | | | 219/505 |
| 5,279,459 A | * | 1/1994 | Single, II | ........... | B60H 1/00842 |
| | | | | | 219/202 |
| 5,513,296 A | * | 4/1996 | Goldstein | ................ | H05B 3/16 |
| | | | | | D23/335 |
| 6,379,242 B1 | * | 4/2002 | Wiseman, Sr. | ......... | A61L 9/122 |
| | | | | | 222/647 |
| 7,643,734 B2 | * | 1/2010 | Wefler | .................... | A61L 9/127 |
| | | | | | 392/390 |
| 9,457,117 B2 | * | 10/2016 | O'Leary | ................. | A61L 9/127 |

(Continued)

OTHER PUBLICATIONS

CN112293122 (Year: 2023).*

(Continued)

*Primary Examiner* — Nathaniel E Wiehe
*Assistant Examiner* — Frederick F Calvetti
(74) *Attorney, Agent, or Firm* — Novoclaims Patent Services LLC; Mei Lin Wong

(57) ABSTRACT

An air supply device with air refreshing and insect repellent function include a housing, which comprises: an air duct unit supported inside the housing having a hollow body defining an air channel; a centrifugal fan received inside the air duct unit; two main air inlets arranged at two opposite sides of the housing; an air outlet arranged at a top portion of the housing and channeled through with the air channel inside the air duct unit at a front side of the housing perpendicular to each of the main air inlets; an auxiliary air inlet arranged at a rear side of the housing opposite to the air outlet; an auxiliary component, which is an aromatherapy component or a mosquito repellent component, connected to the housing at the auxiliary air inlet; and an optional heating component detachably connected to the housing at the main air inlet.

20 Claims, 10 Drawing Sheets

(56) References Cited

U.S. PATENT DOCUMENTS

| | | | | |
|---|---|---|---|---|
| 10,047,973 B2* | 8/2018 | Gao | ............... | F24H 3/0411 |
| 11,493,234 B2* | 11/2022 | Gao | ............... | F04D 29/4226 |
| 2003/0198564 A1* | 10/2003 | Gatley, Jr. | ............... | F04D 25/06 |
| | | | | 417/423.14 |
| 2004/0197091 A1* | 10/2004 | Orr | ............... | F24H 3/0417 |
| | | | | 392/360 |
| 2007/0297773 A1* | 12/2007 | Gao | ............... | F04D 29/582 |
| | | | | 415/177 |
| 2008/0124060 A1* | 5/2008 | Gao | ............... | F24H 9/2071 |
| | | | | 392/365 |
| 2010/0081370 A1* | 4/2010 | Weng | ............... | F24F 13/02 |
| | | | | 454/252 |
| 2012/0304977 A1* | 12/2012 | Gao | ............... | F24H 15/128 |
| | | | | 29/428 |
| 2013/0149956 A1* | 6/2013 | Su | ............... | F24F 1/005 |
| | | | | 454/329 |
| 2013/0334716 A1* | 12/2013 | Ching | ............... | F24F 6/12 |
| | | | | 261/142 |
| 2017/0184316 A1* | 6/2017 | Gao | ............... | F24F 7/007 |
| 2017/0238527 A1* | 8/2017 | Wynalda, Jr. | ............... | A61L 9/12 |
| 2020/0306402 A1* | 10/2020 | Qasem | ............... | A61L 9/032 |
| 2022/0105224 A1* | 4/2022 | Vazquez Alvarez | .... | A61L 9/013 |

OTHER PUBLICATIONS

JP2005348662 (Year: 2023).*
EP2896408 (Year: 2023).*
CN209427184 (Year: 2023).*
WO2013124655 (Year: 2023).*
WO2014043639 (Year: 2023).*

\* cited by examiner

AIR SUPPLY DEVICE WITH AIR REFRESHING AND MOSQUITO REPELLING FUNCTION

BACKGROUND OF THE PRESENT INVENTION

Field of Invention

The present invention relates to an air-conditioning device and, more particularly to an electric air supply device for refreshing air and repelling mosquito, which is capable of blowing refreshing aromatherapy gas and mosquito repellent gas.

Description of Related Arts

Electric fans are well-known household appliances which are widely used because they are inexpensive, easy to operate and has low cost of use. The conventional electric fan uses a motor to drive fan blades to generate air supply function, and can only generate cool air. In winter, in addition to using air conditioners and heating equipment for heating, small-sized, low-cost and portable heaters are also widely used. However, the function of a conventional heater is relatively limited, which has only a single heating function. In addition, the conventional electric fans and heaters are different types of products, each of which is designed for providing one particular function only. A single household may need to purchase two products for cooling and heating purposes, which is not only costly, but also takes up a large amount of space. Also, in order to regulate the indoor air for different purposes, it is necessary to purchase an aromatherapy diffuser, a mosquito repellent device, and etc., which is not only costly, but also inconvenience to use.

SUMMARY OF THE PRESENT INVENTION

An object of the present invention is to solve the above problems and provide an air supply device capable of providing air refreshing function and mosquito repellent function. The air supply device has a small size and is easy to operate, which integrates the different functions of a fan, a heater, an aromatherapy diffuser and a mosquito repellent diffuser in one single device according to the need of a user.

Additional advantages and features of the invention will become apparent from the description which follows, and may be realized by means of the instrumentalities and combinations particular point out in the appended claims.

According to the present invention, the foregoing and other objects and advantages are attained by an air supply device with air refreshing and insect repellent function, comprising: a housing, which comprises:
- an air duct unit supported inside the housing having a hollow body defining an air channel;
- a centrifugal fan received inside the air duct unit; two main air inlets arranged at two opposite sides of the housing;
- an air outlet arranged at a top portion of the housing and channeled through with the air channel inside the air duct unit at a front side of the housing perpendicular to each of the main air inlets;
- an auxiliary air inlet arranged at a rear side of the housing opposite to the air outlet; and
- an auxiliary component, which is an aromatherapy component or a mosquito repellent component, detachably connected to the housing at the auxiliary air inlet.

The air supply device with air refreshing and insect repellent function may further comprises a heating component detachably connected to the housing at one of the main air inlet serving as an optional component for heating air intake from one of the main air inlets.

The housing comprises: a left case member having one the main air inlet; a right case member having one the main air inlet, mated and connected with the left case member; a front case member connected to the left case member and the right case member at a front side of the housing; an inlet grid mounted onto each of the left case member and the right case member at each of the main air inlets; a control knob arranged on the front case member for on/off control and temperature adjustment; and a plurality of positioning sockets provided at an end surface of the left case member.

The auxiliary component, which is an aromatherapy component or a mosquito repellent component, comprises a heating body and a sheet element moveably arranged on a top portion of the heating body, wherein the sheet element is selected from the group consisting of an aroma sheet and a mosquito repellent sheet such that the aroma sheet or the mosquito repellent sheet are interchangeable for use, wherein the heating body is positioned at the auxiliary air inlet.

The heating body comprises a heating body casing formed by an upper case and a lower case mating and connecting to each other, an upper electrode plate, a lower electrode plate, and a PTC heating plate sandwiched between the upper electrode plate and the lower electrode plate and electrically connected to the upper electrode plate and the lower electrode plate, the upper electrode plate and the lower electrode plate are connected to a power source.

A heating temperature of the heating body (PTC heating plate) is 70° C. to 80° C. for heating the aroma sheet, and is 95° C. to 105° C. for heating the mosquito repellent sheet.

The air duct unit comprises an air duct casing and the air channel is inside the air duct casing, wherein the air duct casing is formed by a left air duct member and a right air duct member coupled with the left air duct member, and has a longitudinal section of helical shape, an opening of the air channel faces obliquely upwardly, each of the left air duct member and the right air duct member has a panel protruded upwardly at a top portion thereof, and the air outlet with a cylindrical shape is formed by mating the two panels of the left air duct member and the right air duct member.

The centrifugal fan comprises a fan wheel eccentrically disposed inside the left air duct member of the air duct casing, and a motor disposed inside the right air duct member of the air duct casing and connected to the fan wheel, wherein an outer contour of the fan wheel and an inner wall of the air duct casing of the air duct unit form the air channel that gradually expands from one end to the other end.

The heating component comprises a heating component casing, a heating element channel casing arranged at one end of the heating component casing, a heating element frame affixed at one end portion of the heating element channel casing, a heating element affixed on the heating element frame, and an overheat protector mounted on a top portion of the heating element frame and electrically connected to the heating element, wherein the heating element channel casing comprises a plurality of engaging members spacedly arranged on an end portion thereof, the plurality of engaging members correspond to a plurality of positioning sockets of the left case member, and the heating component is plugged onto the housing through the engaging members and the positioning sockets.

The heating element is a PTC heating element arranged to connect to a power source.

The present invention can effectively solve the problems of single function of existing electric fans and heaters. The present invention can organically combine the electric fan and the heater together to form an integrated air supply device. The user can choose to use the electric fan function or the heater function. The switching and assembling of functional parts are simple, convenient and quick. More importantly, the present invention integrates an aromatherapy diffuser and mosquito repellent device to the integrated air supply device so that it can further provide air refreshing and mosquito-repellent functions into the room while supplying cool or warm air circulation. Thus it can further optimize the indoor air condition and environment, which is beneficial to people's work, life and physical health. The present invention can make the flow and conveyance of wind more smoothly and efficient through the optimized design of the air duct. The present invention also has the characteristics of convenient and fast assembly, small size, high level of portability and easy to use, etc.

Still further objects and advantages will become apparent from a consideration of the ensuing description and drawings. These and other objectives, features, and advantages of the present invention will become apparent from the following detailed description, the accompanying drawings, and the appended claims.

DETAILED DESCRIPTION OF THE PREFERRED EMBODIMENT

Figure 1:
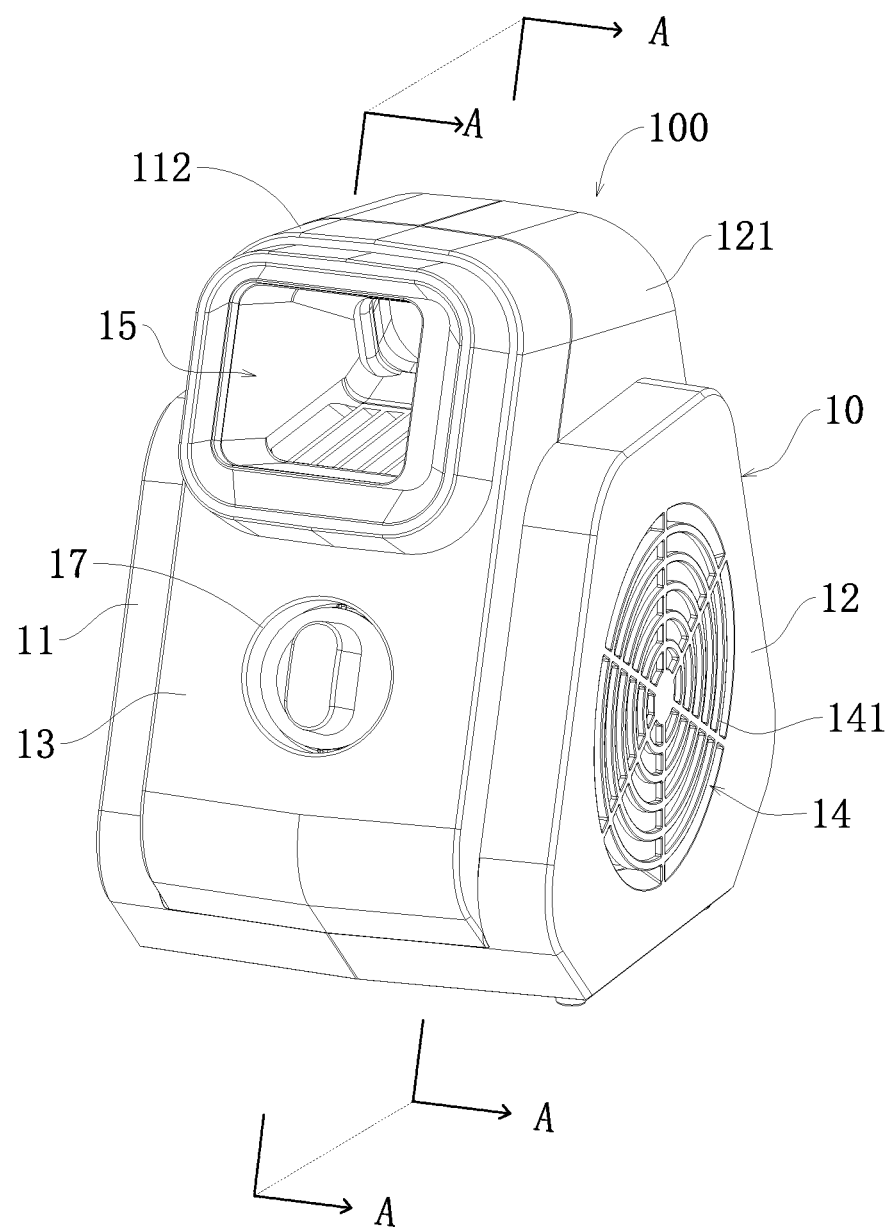
FIG. 1 is a schematic front perspective view of an air supply device according to a preferred embodiment of the present invention.
Figure 2:
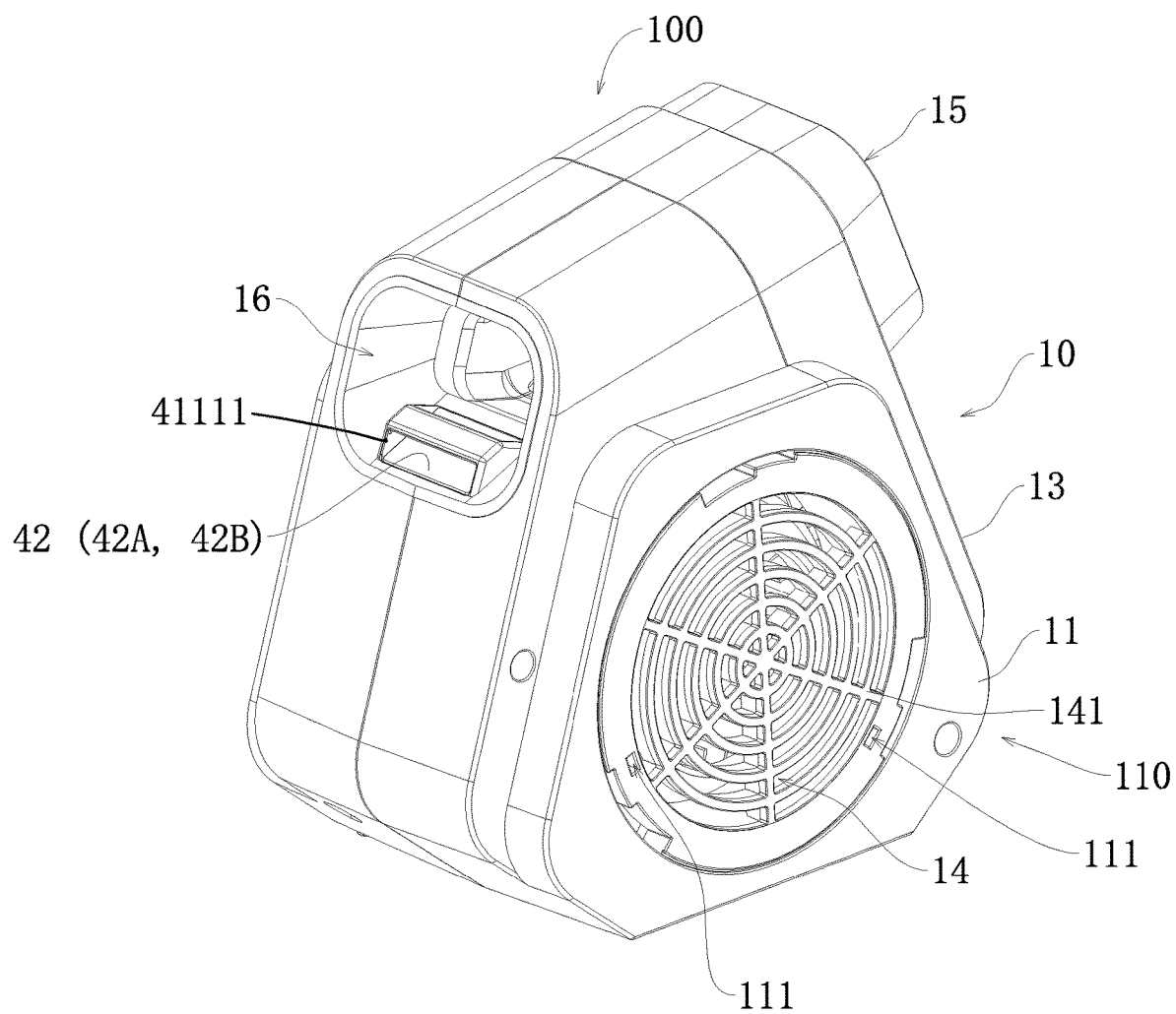
FIG. 2 is a schematic side perspective view of the air supply device according to the above preferred embodiment of the present invention.

The preferred embodiment of the present invention is further described with the accompanying drawings as follows, which is not intended to be limiting.

Referring to FIG. 1 to FIG. 4 of the drawings, an air supply device 100 capable of providing air refreshing function and mosquito repellent function according to a preferred embodiment includes a housing 10, an air duct unit 20, a centrifugal fan 30, a detachable auxiliary component 40 which may be an aromatherapy component 40A or a mosquito repellent component 40B. The present invention can also include an optional heating component 50. The heating component 50 can be added on the basis of the above-mentioned air supply device to form an air supply device with integrated functions of a fan, a heater, an aromatherapy diffuser and a mosquito repellent diffuser in one single device.

Referring FIG. 1 to FIG. 4 of the drawings, the air supply device 100 has a housing 10, the housing 10 is formed by a left case member 11, a right case member 12, and a front case member 13 connecting together. Each of the left case member 11 and the right case member 12 comprises an inlet grid 141 for air intake and has a plurality of screw holes 180 on the edge portion 18 at the inner side of the case member 11, 12. The left case member 11 and the right case member 12 are connected by screws 181 through the screw holes 180. The housing 10 has two main air inlets 14 at two opposite sides respectively for air intake. Air is guided to enter the housing 10 through the two main air inlets 14. The housing 10 has an air outlet 15 at an upper end for air output. The air outlet 15 communicates through the air duct inside the air duct unit 20 and turns to a side perpendicular to the main air inlet 14. In other words, the side at which the air outlet 15 is positioned is perpendicular to the side at which each of the main air inlet 14 is positioned. An auxiliary air inlet 16 is arranged at one end of an opposite side of the air outlet 15. The auxiliary air inlet 16 has a ring-like body having a greater outer opening and a smaller inner opening and is connected to the air outlet 15 by snap-fit connection. Preferably, the auxiliary air outlet 16 has a connecting rim 161 engaging to a connecting groove 151 of the housing 10 at the opposite side of the air outlet 15. When air comes out from the air outlet 15, the negative pressure formed at the auxiliary air inlet 16 causes air to enter the auxiliary air inlet 16. Then the aroma or the mosquito repellent gas generated by the aromatherapy component 40A or the mosquito repellent component 40B after heating will be introduced into the air outlet 15 to exit through the air outlet 15. The tops of the left and right case members 11 and 12 are respectively provided with air outlet baffles 112 and 121 protruding upward and turning inward. When the left case member 11 and the right case member 12 are mated and connected, the air outlet baffles 112 and 121 of the left case member 11 and the right case member 12 are mated to cover the outside of the cylindrical air outlet 15 of the air duct unit. A plurality of positioning sockets 111 are arranged on an end surface 110 of the left case member 11 for connecting the heating component 50. The front case member 13 is snap-fitted and fixed to the front side of the left casing 11 and the right casing 12 with screws. A control knob 17 is provided on the front case member 13 for on/off control and temperature adjustment.

Figure 3:
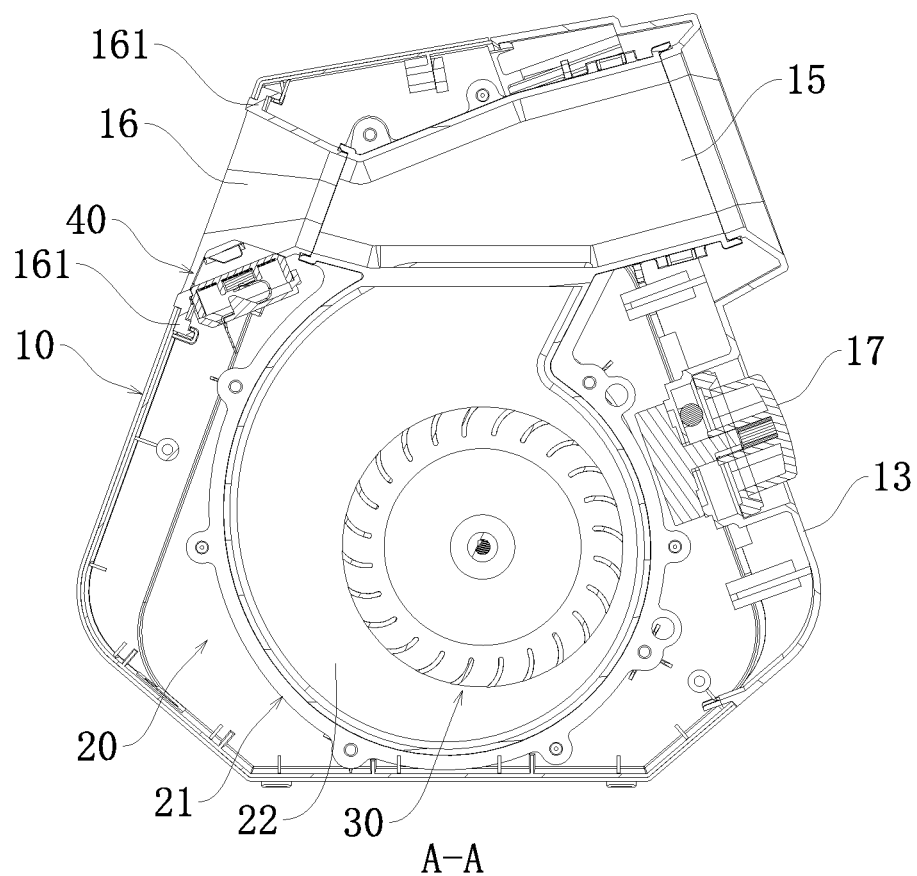
FIG. 3 is a sectional view showing the structure of the air supply device according to the above preferred embodiment of the present invention.
Figure 4:
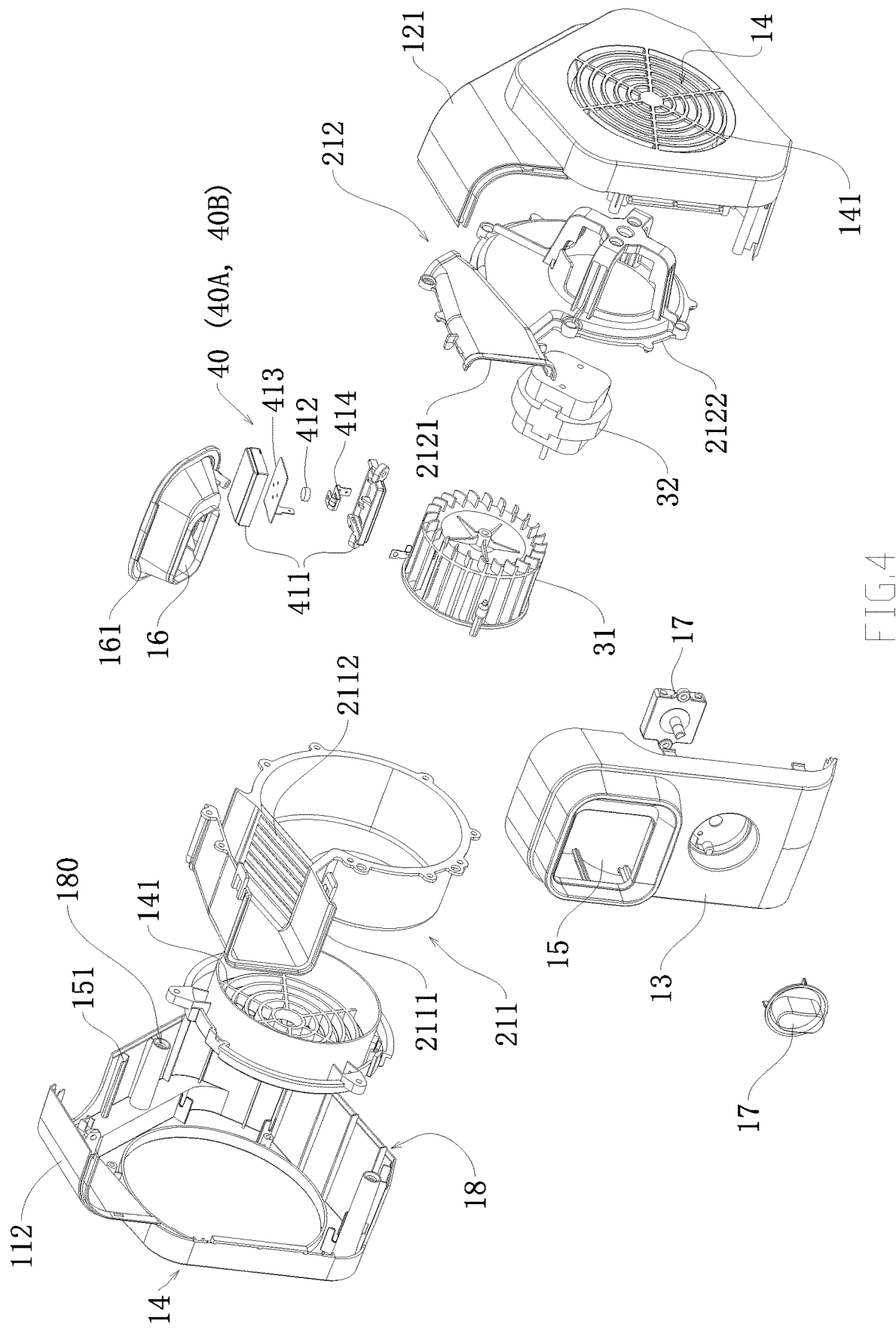
FIG. 4 is an exploded view of the air supply device according to the above preferred embodiment of the present invention.

Referring to FIG. 3 and FIG. 4 of the drawings, the air duct unit 20 is received inside the housing 10 and is arranged for guiding an airflow. The air duct unit 20 comprises an air duct casing 21 and an air channel 22 as defined by the air duct casing 21. The air duct casing 21 is formed by a left air duct member 211 and a right air duct member 212 coupled with the left air duct member 211. The left air duct member 211 has a ring-shaped body defining a top portion, and comprises an outlet grid 2112 at the top portion and a U-shaped panel 2111 protruded upward at an outer side of the outlet grid 2112. The right air duct member 212 has a plate-shaped body defining a top portion, and comprises a motor bracket 2122 at an outer side and a U-shaped panel 2121 protruded upward at the top portion thereof. After the left air duct member 211 and the right air duct member 212 are coupled and connected together, the U-shaped panel 2111 of the left air duct member 211 and the U-shaped panel 2121 of the right air duct member 212 are mated to form the cylindrical air outlet 15. The cylindrical air outlet 15 faces obliquely upward, which can further spread the wind output. As shown in FIG. 3 of the drawings, the longitudinal section of the air duct unit 20 is helical, which makes the resistance of the wind generated by the centrifugal fan 30 in the air duct as small as possible, and the transmission efficiency is higher.

Referring to FIG. 3 and FIG. 4 of the drawings, the centrifugal fan 30 is arranged inside the air duct unit 20. The centrifugal fan 30 comprises a fan wheel 31 and a motor 32. The fan wheel 31 is eccentrically disposed inside the left air duct member 211 of the air duct casing 21, and a wheel shaft of the fan wheel 31 is connected to the motor 32. The outer contour of the fan wheel 31 and the inner wall of the air duct casing 21 of the air duct unit 20 form an air channel 22 that gradually expands from one end to the other end. The wind generated by the fan wheel 31 passes through the air channel 22 and is blown out through the air outlet 15 at the top portion. The motor 32 is disposed in the motor bracket 2122 of the right air duct member 212 of the air duct casing 21 and is connected to the wheel shaft of the fan wheel 31.

Figure 5:
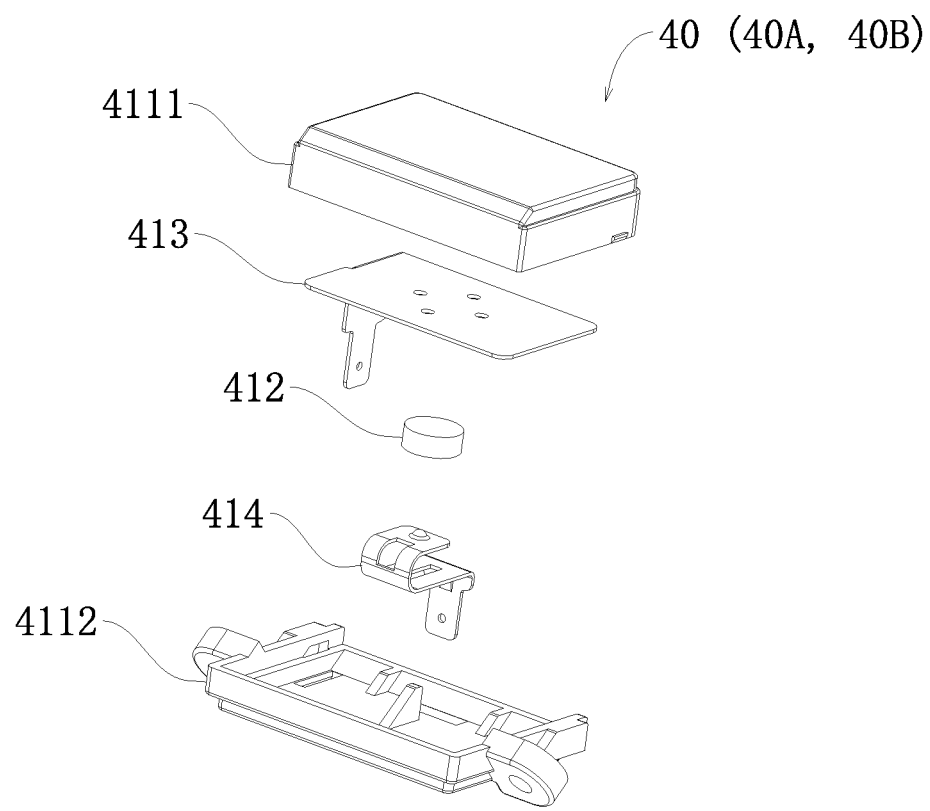
FIG. 5 is an exploded view of an aromatherapy component or a mosquito repellent component of the air supply device according to the above preferred embodiment of the present invention.
Figure 6:
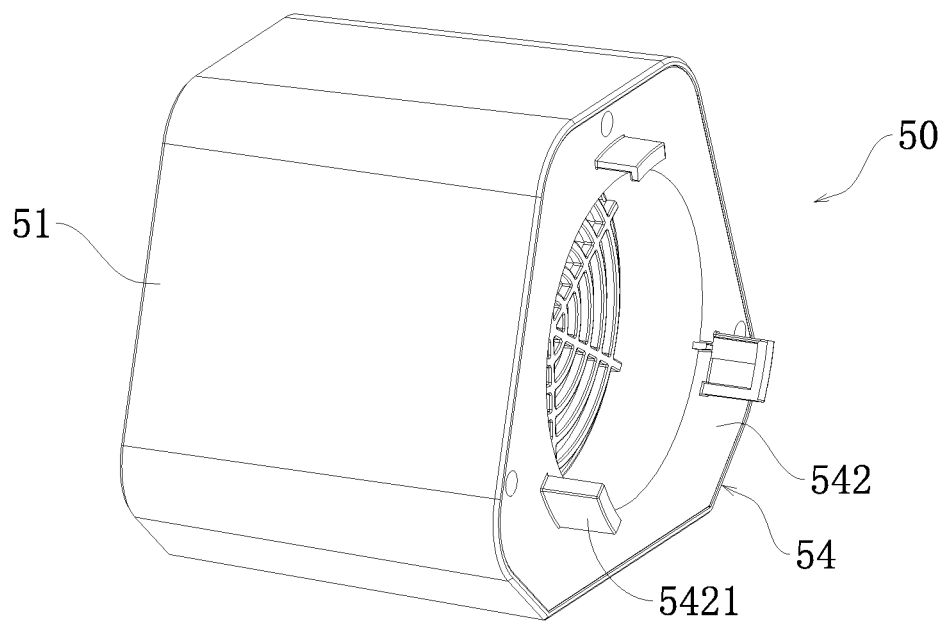
FIG. 6 is a schematic perspective view of a heating component of the air supply device according to the above preferred embodiment of the present invention.
Figure 7:
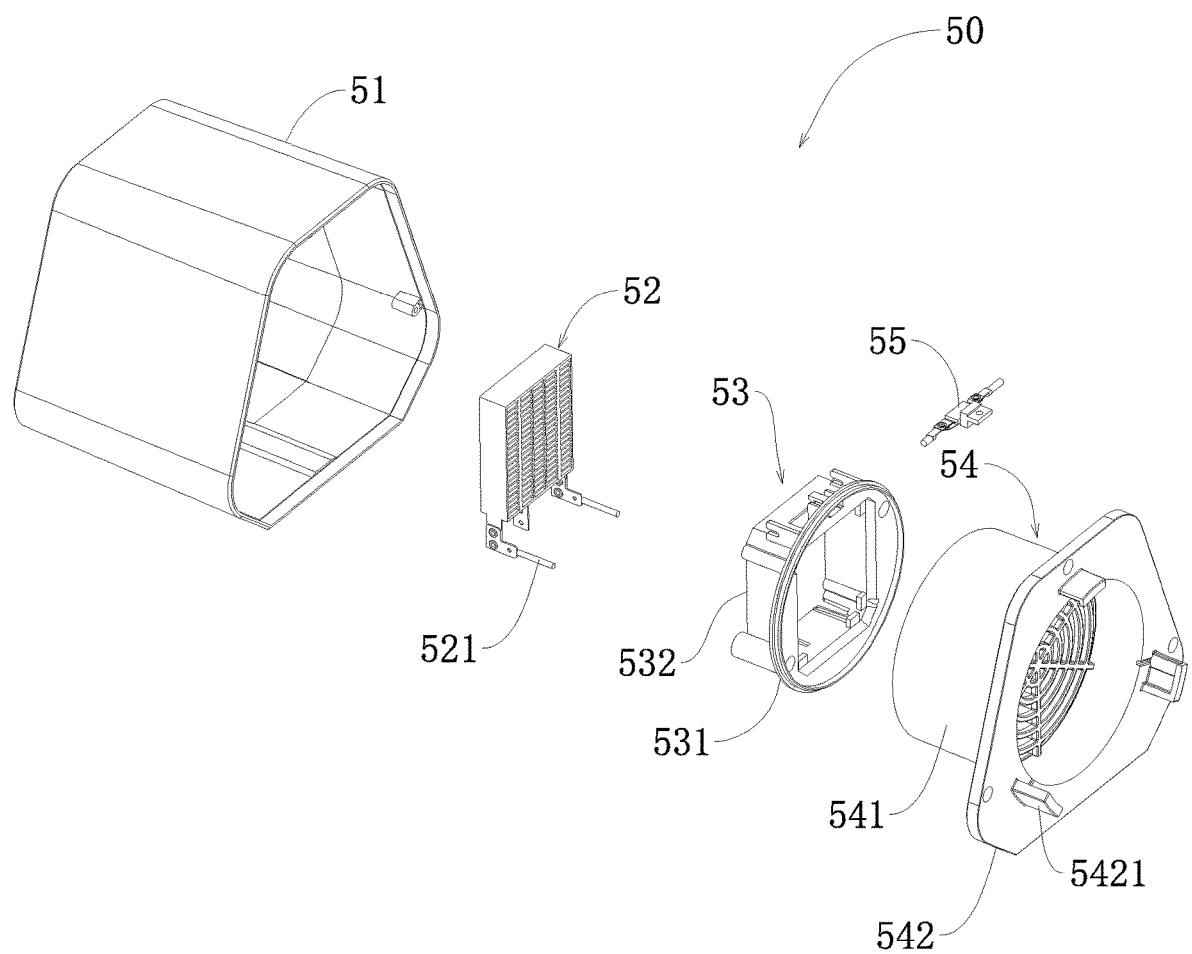
FIG. 7 is an exploded view of the heating component of the air supply device according to the above preferred embodiment of the present invention.
Figure 8:
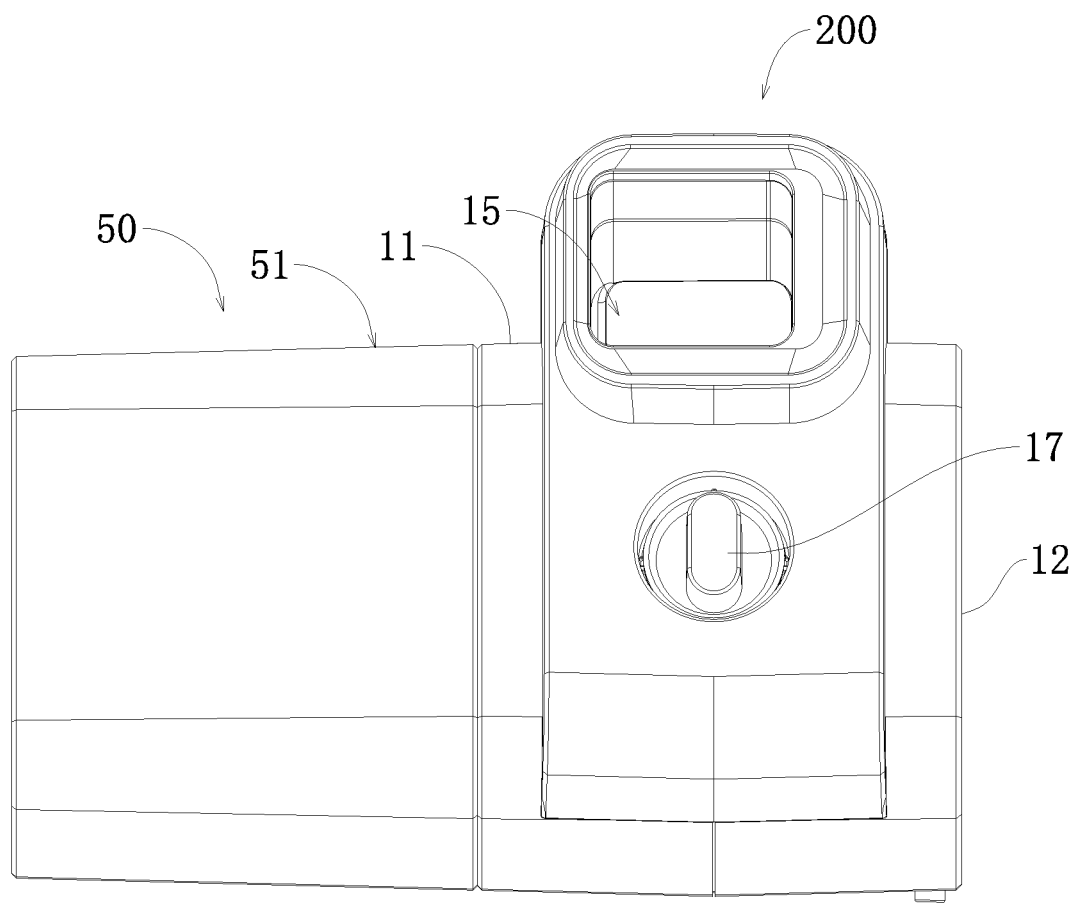
FIG. 8 is a schematic diagram of a heater device provided with the heating component of the air supply device according to the above preferred embodiment of the present invention.

Referring to FIG. 1, FIG. 4 and FIG. 5 of the drawings, the detachable auxiliary component 40, which may be the aromatherapy component 40A for air refreshing or the mosquito repellent component 40B for repelling mosquito, is arranged at the auxiliary air inlet 16. The aromatherapy component 40A and the mosquito repellent component 40B are optional and are interchangeable. The detachable auxiliary component 40 comprises a heating body 41 and a sheet element 42, which can be an aroma sheet 42A or a mosquito repellent sheet 42B. The heating body 41 comprises a heating body casing 411, a PTC heating plate 412, an upper electrode plate 412 and a lower electrode plate 414. The heating body casing 411 is a box-shaped body formed by an upper case 4111 and a lower case 4112 connecting together. The upper case 4111 has a slot 41111 at a top portion thereof arranged for placing an aroma sheet or a mosquito repellent sheet. The PTC heating plate 412, the upper electrode plate 412 and the lower electrode plate 414 are received inside the heating body casing 411. The PTC heating plate 412 is positioned between the upper electrode plate 412 and the lower electrode plate 414 and is electrically connected to the upper electrode plate 412 and the lower electrode plate 414 respectively. The upper electrode plate 412 and the lower electrode plate 414 are connected to a power source. The heating body 41 is positioned at the auxiliary air inlet 16.

The sheet element 42, is moveably placed on the upper part of the heating body 41. When using the aromatherapy function or the mosquito repellent function, the sheet element 42, which is an aroma sheet 42A or a mosquito repellent sheet 42B, can be inserted into the slot 41111, the heating body 41 is switched on, and then the aroma sheet 42A or the mosquito repellent sheet 42B emits vapors when heated, the auxiliary air inlet 16 sucks in air under the action of negative pressure and diffuses the vapors from the aroma sheet 42A or the mosquito repellent sheet 42B into the indoor air to achieve rapid diffusion effect. The aroma gas diffused into the room can have an air refreshing effect, or the mosquito repellent gas can provide mosquito repelling effect. When using the aromatherapy or mosquito repellent function, different PTC heating temperatures can be set. The heating temperature of the PTC heating plate 412 when heating the aroma sheet is 70° C. to 80° C., preferably 75° C. The heating temperature of the mosquito repellent sheet is 95° C. to 105° C., preferably 100° C. The heating temperature is determined by selecting the corresponding PTC heating plate according to the set heating temperature. The heating temperature of the PTC heating plate refers to the surface temperature of the PTC heating plate.

Figure 9:
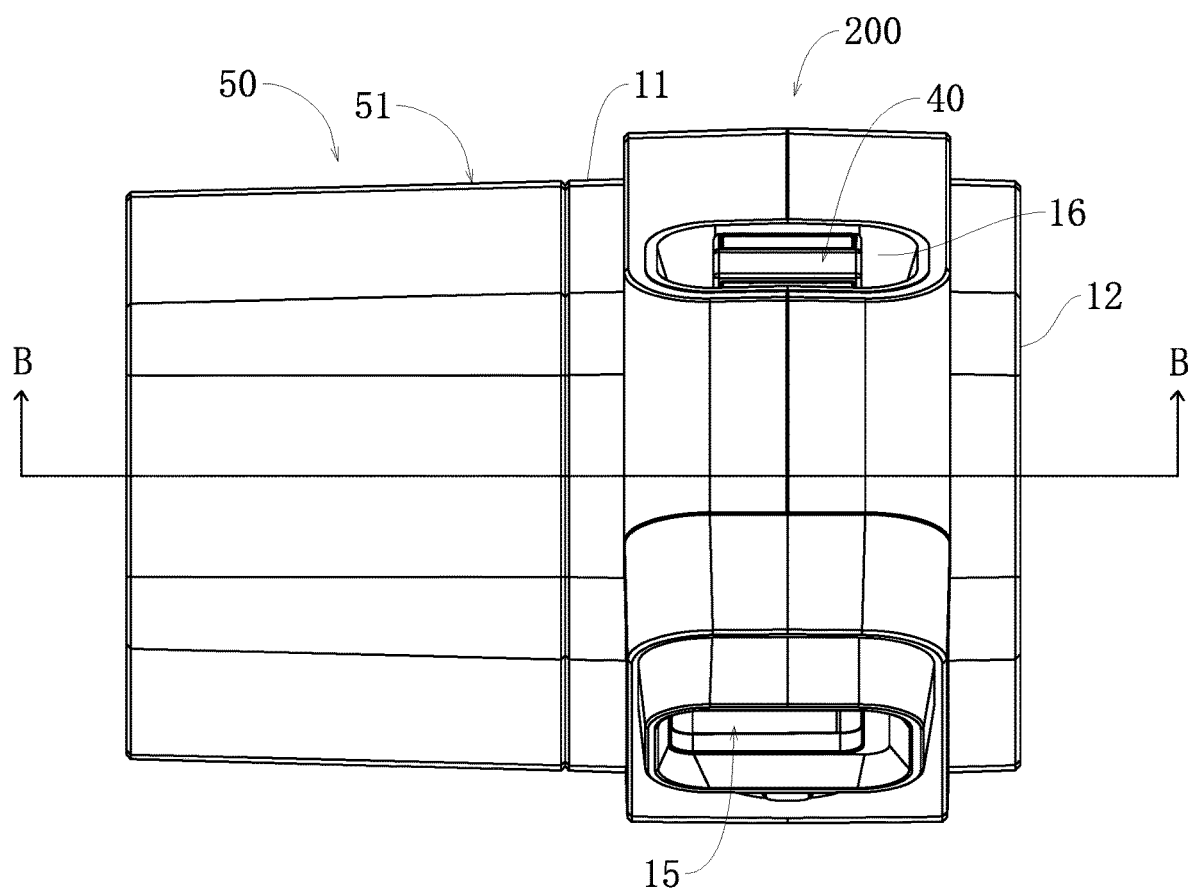
FIG. 9 is a schematic plan view of the heater device provided with the heating component of the air supply device according to the above preferred embodiment of the present invention.
Figure 10:
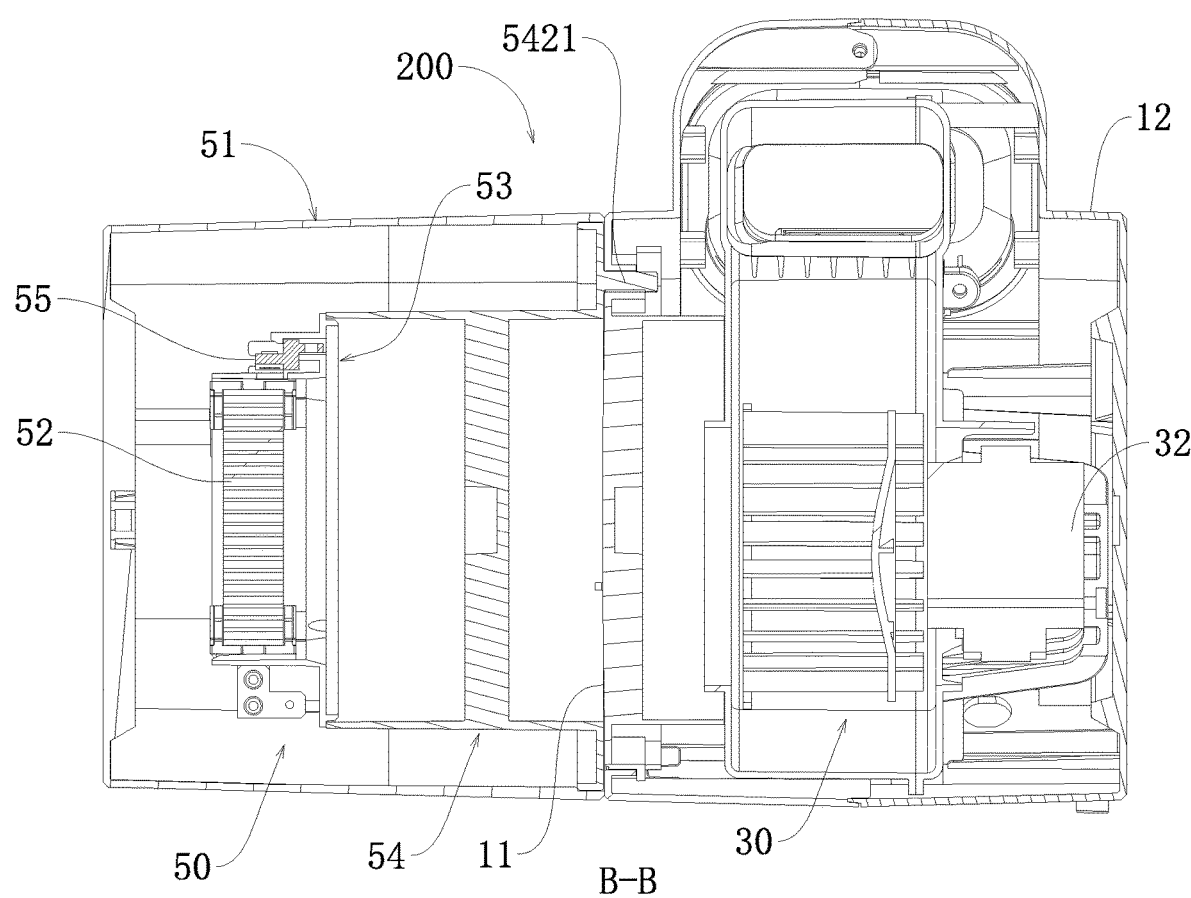
FIG. 10 is a sectional view of the heater device provided with the heating component of the air supply device according to the above preferred embodiment of the present invention.
Figure 11:
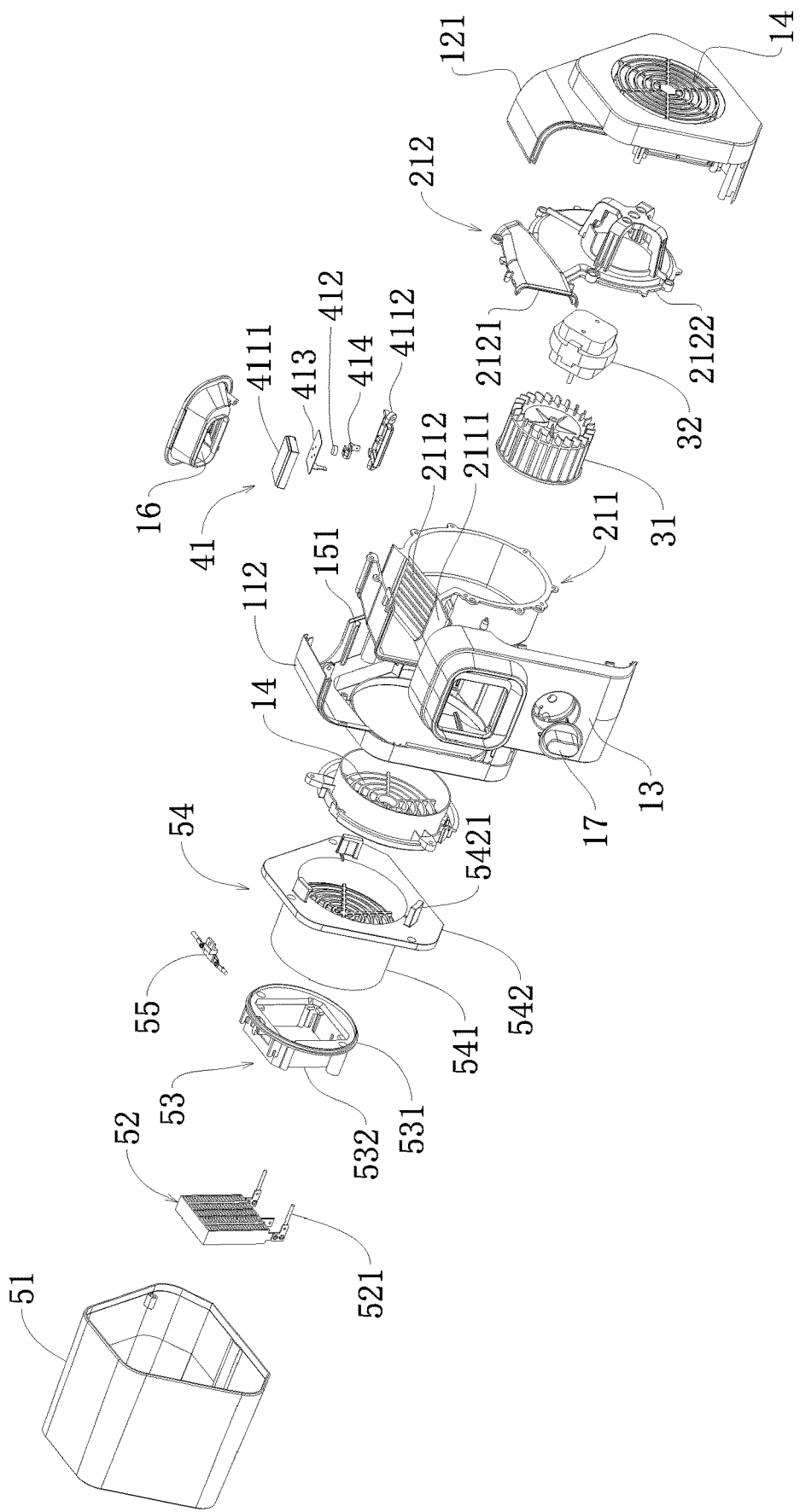
FIG. 11 is an exploded view of the heater device provided with the heating component of the air supply device according to the above preferred embodiment of the present invention.

The air supply device according to a preferred embodiment of the present invention can be embodied as a heater 200. In particular, the heating component 50 can be added to one side of the housing 10 to form the heater 200. Referring to FIG. 6 to FIG. 11 of the drawings, the heating component 50 comprises a heating component casing 51, a heating element 52, a heating element frame 53, a heating element channel casing 54 and an overheat protector 55. The heating element 52 is a PTC heating element, which is arranged to connect to a power source. The PTC heating element 52 is fixed on the heating element frame 53, and an electrode plate 521 is provided at the bottom thereof for connecting to the power source. The heating element frame 53 has a circular connecting portion 531 and a rectangular frame 532 corresponding to the shape of the PTC heating element 52. The connecting portion 531 is fixed to the end of the heating element channel casing 54 by screws. The PTC heating element 52 is snap-fitted inside the rectangular frame 532. The overheat protector 55 is mounted on the top of the heating element frame 53 and is electrically connected to the heating element 52 so that the power source is cut off in the event of short circuit or overload. The heating element channel casing 54 comprises a cylindrical casing 541 and a connecting panel 542 provided at one end portion thereof. The casing 541 communicates with the inner side of the air duct unit 20. The connecting panel 542 comprises a plurality of engaging members 5421 spacedly provided on the connecting panel 542. The plurality of engaging members 5421 correspond to the plurality of positioning sockets 111 of the left case member 11. The heating component 50 is connected to the housing 10 through the engaging members 5421 and the positioning sockets 111. Preferably, the heating component 50 is plugged onto the housing 10 through the engaging members 5421 to secure into position easily and conveniently. By optionally installing the heating component 50, the air supply device 100 can be easily expanded into a heater 200. The expanded form of the air supply device 100, the heater 200, is shown in FIG. 9 to FIG. 11 of the drawings.

When the heating component 50 is in operation, the heat generated by the PTC heating element passes through the heating element channel casing 54 to enter into the air duct unit 20, and then heated air is sent out through the centrifugal fan 30.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An air supply device with air refreshing and insect repellent function, comprising:
   a housing, which comprises:
   an air duct unit supported inside said housing having a hollow body defining an air channel;
   a centrifugal fan received inside said air duct unit;
   two main air inlets arranged at two opposite sides of said housing;
   an air outlet arranged at a top portion of said housing and channeled through with the air channel inside said air duct unit at a front side of said housing perpendicular to each of said main air inlets;
   an auxiliary air inlet arranged at a rear side of said housing opposite to said air outlet; and
   an auxiliary component, which is an aromatherapy component or a mosquito repellent component, detachably connected to said housing at said auxiliary air inlet.

2. The air supply device with air refreshing and insect repellent function according to claim 1, further comprising a heating component detachably connected to said housing at one of said main air inlet serving as an optional component for heating air intake from one of said main air inlets.

3. The air supply device with air refreshing and insect repellent function according to claim 2, wherein said housing comprises:
   a left case member having one said main air inlet;
   a right case member having one said main air inlet, mated and connected with said left case member;
   a front case member connected to said left case member and said right case member at a front side of said housing;
   an inlet grid mounted onto each of said left case member and said right case member at each of said main air inlets;
   a control knob arranged on said front case member for on/off control and temperature adjustment; and
   a plurality of positioning sockets provided from one end surface of said left case member.

4. The air supply device with air refreshing and insect repellent function according to claim 3, said auxiliary component comprises a heating body and a sheet element moveably arranged on a top portion of said heating body, wherein said sheet element is selected from the group consisting of an aroma sheet and a mosquito repellent sheet such that the aroma sheet or the mosquito repellent sheet are interchangeable for use, wherein said heating body is positioned at said auxiliary air inlet.

5. The air supply device with air refreshing and insect repellent function according to claim 4, wherein said heating body comprises a heating body casing formed by an upper case and a lower case mating and connecting to each other, an upper electrode plate, a lower electrode plate, and a PTC heating plate sandwiched between said upper electrode plate and said lower electrode plate and electrically connected to said upper electrode plate and said lower electrode plate, said upper electrode plate and said lower electrode plate are connected to a power source.

6. The air supply device with air refreshing and insect repellent function according to claim 5, wherein a heating temperature of said PTC heating plate is 70° C. to 80° C. for heating said aroma sheet, and is 95° C. to 105° C. for heating said mosquito repellent sheet.

7. The air supply device with air refreshing and insect repellent function according to claim 5, wherein said air duct unit comprises an air duct casing and said air channel is inside said air duct casing, wherein said air duct casing is formed by a left air duct member and a right air duct member coupled with said left air duct member, and has a longitudinal section of helical shape, an opening of said air channel faces obliquely upwardly, each of said left air duct member and said right air duct member has a panel protruded upwardly at a top portion thereof, and said air outlet with a cylindrical shape is formed by mating said two panels of said left air duct member and said right air duct member.

8. The air supply device with air refreshing and insect repellent function according to claim 7, said centrifugal fan comprises a fan wheel eccentrically disposed inside said left air duct member of said air duct casing, and a motor disposed inside said right air duct member of said air duct casing and connected to said fan wheel, wherein an outer contour of said fan wheel and an inner wall of said air duct casing of said air duct unit form said air channel that gradually expands from one end to the other end.

9. The air supply device with air refreshing and insect repellent function according to claim 8, said heating component comprises a heating component casing, a heating element channel casing arranged at one end of said heating component casing, a heating element frame affixed at one end portion of said heating element channel casing, a heating element affixed on said heating element frame, and an overheat protector mounted on a top portion of said heating element frame and electrically connected to said heating element, wherein said heating element channel casing comprises a plurality of engaging members spacedly arranged on an end portion thereof, said plurality of engaging members correspond to a plurality of positioning sockets of said left case member, and said heating component is plugged onto said housing through said engaging members and said positioning sockets.

10. The air supply device with air refreshing and insect repellent function according to claim 9, wherein said heating element is a PTC heating element arranged to connect to a power source.

11. The air supply device with air refreshing and insect repellent function according to claim 3, said heating component comprises a heating component casing, a heating element channel casing arranged at one end of said heating component casing, a heating element frame affixed at one end portion of said heating element channel casing, a heating element affixed on said heating element frame, and an overheat protector mounted on a top portion of said heating element frame and electrically connected to said heating element, wherein said heating element channel casing comprises a plurality of engaging members spacedly arranged on an end portion thereof, said plurality of engaging members correspond to a plurality of positioning sockets of said left case member, and said heating component is plugged onto said housing through said engaging members and said positioning sockets.

12. The air supply device with air refreshing and insect repellent function according to claim 11, wherein said heating element is a PTC heating element arranged to connect to a power source.

13. The air supply device with air refreshing and insect repellent function according to claim 2, said auxiliary component comprises a heating body and a sheet element moveably arranged on a top portion of said heating body, wherein said sheet element is selected from the group consisting of an aroma sheet and a mosquito repellent sheet such that the aroma sheet or the mosquito repellent sheet are interchangeable for use, wherein said heating body is positioned at said auxiliary air inlet.

14. The air supply device with air refreshing and insect repellent function according to claim 13, wherein said heating body comprises a heating body casing formed by an upper case and a lower case mating and connecting to each other, an upper electrode plate, a lower electrode plate, and a PTC heating plate sandwiched between said upper electrode plate and said lower electrode plate and electrically connected to said upper electrode plate and said lower electrode plate, said upper electrode plate and said lower electrode plate are connected to a power source.

15. The air supply device with air refreshing and insect repellent function according to claim 14, wherein a heating temperature of said PTC heating plate is 70° C. to 80° C. for heating said aroma sheet, and is 95° C. to 105° C. for heating said mosquito repellent sheet.

16. The air supply device with air refreshing and insect repellent function according to claim 15, wherein said air duct unit comprises an air duct casing and said air channel is inside said air duct casing, wherein said air duct casing is formed by a left air duct member and a right air duct member coupled with said left air duct member, and has a longitudinal section of helical shape, an opening of said air channel faces obliquely upwardly, each of said left air duct member and said right air duct member has a panel protruded upwardly at a top portion thereof, and said air outlet with a cylindrical shape is formed by mating said two panels of said left air duct member and said right air duct member.

17. The air supply device with air refreshing and insect repellent function according to claim 16, said centrifugal fan comprises a fan wheel eccentrically disposed inside said left air duct member of said air duct casing, and a motor disposed inside said right air duct member of said air duct casing and connected to said fan wheel, wherein an outer contour of said fan wheel and an inner wall of said air duct casing of said air duct unit form said air channel that gradually expands from one end to the other end.

18. The air supply device with air refreshing and insect repellent function according to claim 13, wherein a heating temperature of said heating body is 70° C. to 80° C. for heating said aroma sheet, and is 95° C. to 105° C. for heating said mosquito repellent sheet.

19. The air supply device with air refreshing and insect repellent function according to claim 1, wherein said air duct unit comprises an air duct casing and said air channel is inside said air duct casing, wherein said air duct casing is formed by a left air duct member and a right air duct member coupled with said left air duct member, and has a longitudinal section of helical shape, an opening of said air channel faces obliquely upwardly, each of said left air duct member and said right air duct member has a panel protruded upwardly at a top portion thereof, and said air outlet with a cylindrical shape is formed by mating said two panels of said left air duct member and said right air duct member.

20. The air supply device with air refreshing and insect repellent function according to claim 19, said centrifugal fan comprises a fan wheel eccentrically disposed inside said left air duct member of said air duct casing, and a motor disposed inside said right air duct member of said air duct casing and connected to said fan wheel, wherein an outer contour of said fan wheel and an inner wall of said air duct casing of said air duct unit form said air channel that gradually expands from one end to the other end.

\* \* \* \* \*